(12) United States Patent
Heath et al.

(10) Patent No.: US 8,970,381 B2
(45) Date of Patent: Mar. 3, 2015

(54) SYSTEM AND METHOD FOR COORDINATED HEALTH MONITORING, EMERGENCY RESPONSE, AND MEDICAL RECORD DELIVERY

(71) Applicants: Chester Heath, Boca Raton, FL (US); Noel J. Guillama, Wellington, FL (US)

(72) Inventors: Chester Heath, Boca Raton, FL (US); Noel J. Guillama, Wellington, FL (US)

(73) Assignees: The Quantum Group, Inc., Lake Worth, FL (US); Synabee, Inc., Wellington, FL (US); Noel J. Guillama, Wellington, FL (US)

( * ) Notice: Subject to any disclaimer, the term of this patent is extended or adjusted under 35 U.S.C. 154(b) by 199 days.

(21) Appl. No.: 13/770,301

(22) Filed: Feb. 19, 2013

(65) Prior Publication Data
US 2013/0166323 A1    Jun. 27, 2013

Related U.S. Application Data

(63) Continuation-in-part of application No. 12/535,498, filed on Aug. 4, 2009, now Pat. No. 8,378,831, and a continuation-in-part of application No. 13/302,557, filed on Nov. 22, 2011, now Pat. No. 8,823,500, which
(Continued)

(51) Int. Cl.
*G08B 23/00*    (2006.01)
*G06F 19/00*    (2011.01)
(Continued)

(52) U.S. Cl.
CPC .............. *G06F 19/322* (2013.01); *G06Q 50/22* (2013.01); *G06Q 50/24* (2013.01); *G08B 25/08* (2013.01); *A61B 5/0002* (2013.01); *A61B 5/0205* (2013.01); *A61B 5/117* (2013.01); *A61B 2505/01* (2013.01)
USPC .......................... 340/573.1; 455/456.3; 705/3

(58) Field of Classification Search
CPC . G06Q 50/22; G06F 19/3431; G06F 19/3437; G06F 19/322
USPC ........... 340/573.1; 455/456.1, 456.3; 705/2, 3
See application file for complete search history.

(56) References Cited

U.S. PATENT DOCUMENTS

| 4,617,557 A | 10/1986 | Gordon |
| 5,412,372 A | 5/1995 | Parkhurst et al. |

(Continued)

OTHER PUBLICATIONS

International Search Report and the Written Opinion of the ISA mailed on Nov. 6, 2012 in International Application No. PCT/US12/52404. (9 pages).

(Continued)

*Primary Examiner* — John A Tweel, Jr.
(74) *Attorney, Agent, or Firm* — Novak Druce Connolly Bove + Quigg LLP

(57) ABSTRACT

A computer-based system for providing coordinated health monitoring, emergency response, and medical record delivery. The system can include computing devices configured to process emergency-related indicators and data. The system can also include monitoring devices communicatively linked to the computing devices. The monitoring devices can be configured to monitor a particular area for the emergency-related indicators and data, wherein the monitoring devices detect speech, sounds, images and other detectable emergency-related indicators. The monitoring devices can also be configured to transmit the emergency-related indicators and data to the computing devices. Furthermore, the system can include a module linked to the monitoring devices and configured to execute on the computing devices. The module can analyze the transmitted emergency-related indicators and data to determine whether there is an emergency, communicate with a monitoring service to validate that an emergency exists, and provide access to patient records to authorized personnel, when an emergency exists.

19 Claims, 3 Drawing Sheets

Related U.S. Application Data is a continuation-in-part of application No. 12/470,550, filed on May 22, 2009, now Pat. No. 8,154,390, application No. 13/770,301, which is a continuation-in-part of application No. PCT/US2012/052404, filed on Aug. 25, 2012.

(60) Provisional application No. 61/086,612, filed on Aug. 6, 2008, provisional application No. 61/527,278, filed on Aug. 25, 2011, provisional application No. 61/635,910, filed on Apr. 20, 2012.

(51) Int. Cl.
  *G06Q 50/22* (2012.01)
  *G06Q 50/24* (2012.01)
  *A61B 5/0205* (2006.01)
  *G08B 25/08* (2006.01)
  *A61B 5/00* (2006.01)
  *A61B 5/117* (2006.01)

(56) References Cited

U.S. PATENT DOCUMENTS

| | | | |
|---|---|---|---|
| 5,441,047 A | 8/1995 | David et al. | |
| 5,842,978 A | 12/1998 | Levy | |
| 5,963,136 A | 10/1999 | O'Brien | |
| 6,221,010 B1 | 4/2001 | Lucas | |
| 6,380,858 B1 | 4/2002 | Yarin et al. | |
| 6,562,001 B2 | 5/2003 | Lebel et al. | |
| 6,670,885 B2 | 12/2003 | Kosaka | |
| 6,973,371 B1 | 12/2005 | Benouali | |
| 7,230,521 B2 | 6/2007 | Terenna | |
| 7,366,675 B1 | 4/2008 | Walker et al. | |
| 7,755,478 B2 | 7/2010 | Niemiec et al. | |
| 7,928,835 B1 | 4/2011 | Jovanov et al. | |
| 7,956,727 B2 | 6/2011 | Loncar | |
| 2008/0098313 A1 | 4/2008 | Pollack | |
| 2008/0102856 A1 | 5/2008 | Fortescue et al. | |
| 2008/0188261 A1 | 8/2008 | Arnone | |
| 2008/0215623 A1 | 9/2008 | Ramer | |
| 2009/0215469 A1 | 8/2009 | Fisher | |
| 2013/0122476 A1* | 5/2013 | Guillama et al. | 434/247 |
| 2014/0164012 A1* | 6/2014 | Guillama et al. | 705/2 |

OTHER PUBLICATIONS

Non Final Office Action (USPTO) mailed on Jul. 15, 2011 in U.S. Appl. No. 12/470,550. (13 pages).

Non Final Office Action (USPTO) mailed on Mar. 8, 2012 in U.S. Appl. No. 12/535,498. (11 pages).

* cited by examiner

SYSTEM AND METHOD FOR COORDINATED HEALTH MONITORING, EMERGENCY RESPONSE, AND MEDICAL RECORD DELIVERY

CROSS-REFERENCE TO RELATED APPLICATIONS

This application claims the benefit of U.S. patent application Ser. No. 12/535,498, filed Aug. 4, 2009, which claims priority to U.S. Provisional Patent Application No. 61/086,612, which was filed Aug. 6, 2008, and which is incorporated herein in its entirety. This application further claims the benefit of U.S. Provisional Patent Application No. 61/635,910, filed Apr. 20, 2012. This application also claims the benefit of U.S. patent application Ser. No. 13/302,557, filed Nov. 22, 2011, which claims priority to U.S. patent application Ser. No. 12/470,550, filed May 22, 2009. This application further claims priority to International Patent Application No. PCT/US12/52404, filed Aug. 25, 2012, which claims priority to U.S. Provisional Patent Application No. 61/527,278, filed Aug. 25, 2011. The contents of each of the foregoing are herein incorporated by reference in their entirety.

FIELD OF THE INVENTION

The present invention is related to the field of health care, and more particularly, to computer-based systems and methods for providing coordinated health monitoring, emergency response, disease and health care management, and medical records delivery.

BACKGROUND OF THE INVENTION

Significant advances in medical technologies, improved medical procedures, and ever more highly-skilled emergency response teams have provided great benefits, allowing individuals to live longer and more enjoyable lives, while also mitigating the number and severity of medical complications experienced by individuals. Despite these considerable advances, difficulties inherent in detecting and assisting at the earliest opportunity an individual experiencing a medical emergency remains a major obstacle to providing optimal healthcare.

An individual undergoing a medical emergency is often times too incapacitated to call emergency services, take a desperately-needed medication, or even alert anyone who happens to be nearby that the emergency is occurring. Too often, by the time someone who can capably assist the individual is made aware of the situation and is able to respond, the emergency has progressed to a critical stage resulting in permanent impairment or even death of the individual.

An important complicating factor is that an emergency team seeking to assist the individual is often times forced to treat the individual without any knowledge of the individual's medical history and without any access to relevant medical records. As a result, such individuals all too often suffer irreversible complications, irreparable harm, and even death. Even under the best of circumstances, whenever a healthcare provider must treat an individual without adequate knowledge of the individual's medical history and access to the individual's medical records, the result can be unnecessary, inadequate, or even injurious treatment of the individual.

As a result, there is a need for more effective and efficient mechanisms for providing emergency detection and emergency response to individuals experiencing medical emergencies. More generally, there is a need for more effective and efficient mechanisms for providing healthcare providers with access to critical medical histories and records so as to improve diagnosis and treatment of a wide array of medical conditions. Furthermore, there is a need for mechanisms to more effectively and efficiently coordinate health monitoring, to speed up emergency response times, assist in disease management and control, and ensure the rapid delivery of medical records and other critical information to healthcare providers.

SUMMARY OF THE INVENTION

The present invention is directed to systems and methods for providing coordinated health monitoring and emergency detection. The invention is also directed to systems and methods that can speed up emergency response times as well as increasing the speed and security with which medical records and other critical information are delivered to healthcare providers.

One embodiment of the invention is a computer-based system for providing coordinated health monitoring, emergency response, and medical record delivery. The system can include one or more computing devices configured to process emergency-related indicators and data. The system can also include one or more monitoring devices communicatively linked to the one or more computing devices. The one or more monitoring devices can be configured to monitor a particular area for the emergency-related indicators and data, wherein the one or more monitoring devices detect one or more among speech, sounds, images, and other detectable emergency-related indicators. The one or more monitoring devices can also be configured to transmit the emergency-related indicators and data to the one or more computing devices. Furthermore, the system can include a module communicatively linked to the one or more monitoring devices and configured to execute on the one or more computing devices. The module can be configured to analyze the transmitted emergency-related indicators and data to determine whether there is an emergency, communicate with a monitoring service to validate that an emergency exists, and provide access to patient records to authorized personnel, based upon whether an emergency exists.

Another embodiment of the invention is a computer-based method for providing coordinated health monitoring, emergency response, and medical record delivery. The method can include monitoring a particular area for emergency-related indicators and data by utilizing one or more monitoring devices, wherein the one or more monitoring devices detect one or more of speech, sounds, images, and other detectable emergency-related indicators. The method can also include transmitting the emergency-related indicators and data to one or more computing devices, wherein the one or more computing devices are communicatively linked to the one or more monitoring devices. Additionally, the method can include analyzing the transmitted emergency-related indicators and data to determine whether there is an emergency, wherein the analysis can be performed by the one or more computing devices. The method can further include communicating with a monitoring service to validate that an emergency exists. Moreover, the method can also include providing access to patient records to authorized personnel, based upon whether an emergency exists.

Yet another embodiment of the invention is a computer-readable medium which contains computer-readable code that when loaded on a computer causes the computer to monitor a particular area for emergency-related indicators and data by utilizing one or more monitoring devices, wherein the one or more monitoring devices detect one or more of speech, sounds, images, and other detectable emergency-related indicators; to transmit the emergency-related indicators and data to one or more computing devices, wherein the one or more computing devices are communicatively linked to the one or more monitoring devices; to analyze the transmitted emergency-related indicators and data to determine whether there is an emergency, wherein the analysis is performed by the one or more computing devices; to communicate with a monitoring service to validate that an emergency exists; and to provide access to patient records to authorized personnel, based upon whether an emergency exists.

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

Figure 1:
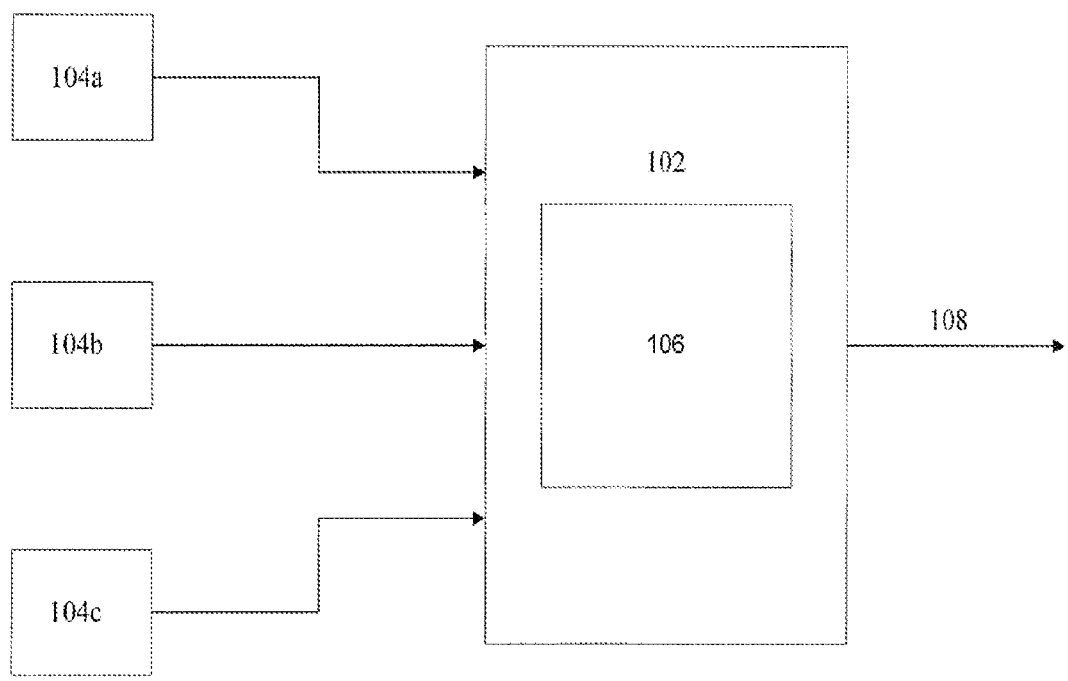
FIG. 1 is a schematic view of a system for providing coordinated health monitoring, emergency response, and medical record delivery, according to one embodiment of the invention.

Referring initially to FIG. 1, a system 100 for providing coordinated health monitoring, emergency response, and medical record delivery, according to one embodiment of the invention, is schematically illustrated. The system can include one or more computing devices 102 configured to process emergency-related indicators and data. For example, the one or more computing devices 102 can include, but is not limited to, a desktop computer, laptop, personal digital assistants (PDA), or similar type computing device or communication device having data processing capabilities (e.g., a controller, registers, logic gates, and other logic-based processing circuitry). The system 100 further can include one or more monitoring devices 104a-c communicatively linked to the one or more computing devices 102. Although illustratively, only one computing device 102 and three monitoring devices 104a-c are shown, it will be readily apparent to one of ordinary skill based on the description that a greater number of computing devices and a greater or lesser number of databases can be utilized.

The system 100 can also include a module 106 that is communicatively linked to the one or more monitoring devices 104a-c and configured to execute on the one or more computing devices 102. Alternatively, the module 106 can be implemented in hardwired, dedicated circuitry for performing the operative functions described herein. In another embodiment, the module 106 can be implemented in a combination of logic-based data processing circuitry and computer-readable code configured to execute on a particular computing machine.

Operatively, the system 100 is configured to respond whenever a person exhibits the symptoms of, or is undergoing, an emergency. The one or more monitoring devices 104a-c can monitor predetermined conditions within a particular area for emergency-related indicators and data. The one or more monitoring devices 104a-c can detect one or more among speech, sounds, images, and other detectable emergency-related indicators. For example, if a person is experiencing significant pain, one or more of the monitoring devices 104a-c can be configured to sense and record sounds and/or images that are indicative or suggestive of an emergency condition. In a particular embodiment, the one or more monitoring devices 104a-c can digitize and encrypt data captured and/or generated in response to the detection of a possible emergency condition.

After sensing emergency-related indicators and after capturing and/or generating data in response thereto, the one or more monitoring devices 104a-c can transmit the emergency-related indicators and data to the one or more computing devices 102. Once the module 106 receives the emergency-related indicators and data, the module 106 can analyze the transmitted emergency-related indicators and data to determine whether there is an emergency. For enhanced validation, the module 106 can communicate with a monitoring service (not explicitly shown) to verify that an emergency exists. If an actual emergency exists or is determined to be likely occurring, the module 106 can provide emergency responders or other authorized personnel access to patient records. For example, an Internet link can be provided to emergency medical personnel or emergency room services to connect to the monitored individual's records. The monitored individual would agree in advance to the release of records in the event of an emergency.

According to a particular embodiment, the one or more monitoring devices 104a-c can comprise one or more among a microphone, a speaker, a smoke detector, a heat detector, a device enabling encryption of the emergency-related indicators and data, a camera, a video camera, an intercom, a baby monitor, and a motion sensor. Additionally, the one or more monitoring devices 104a-c and the one or more computing devices 102 can be adapted to be portable so as to be carried by an individual and to be communicatively linked to one or more of monitoring services, offices, WiFi enabled facilities, telephone services, and mobile services. In a particular embodiment, the system 100 can be configured to implement one or more measures to ensure that the communications link and data exchanged over the link are protected against illicit and/or unwanted intrusion and access.

In another embodiment, the system 100 can include health-monitoring sensors, wherein the health-monitoring sensors can detect one or more among blood pressure, temperature, heart-rate, and other health-related patient metrics. For example, if a person is experiencing a fever, a sensor could determine that the person's body temperature is too high and relay the reading to the one or more computing devices 102. According to another embodiment, the module 106 can communicatively link to emergency services and signal an alarm to indicate that an emergency is occurring. For example, if a person has a severe wound, the system could sound an alarm so as to alert those nearby and/or send a signal to emergency services to assist the person.

In one embodiment, the module 106 can store and forward a record of the emergency-related indicators and data to one or more of the monitoring service and an emergency service. As an illustration, as the one or more monitoring devices 104a-c sense emergency-related data, the data can be stored to serve as a patient history and forwarded to appropriate emergency personnel. According to still another embodiment, the system 100 can integrate drug dispensing devices, wherein the drug dispensing devices administer drugs so as to enable remote medical maintenance. If a person is undergoing an emergency, which can be treated through the use of drugs, the drug dispensing devices can be remotely controlled so as to enable prompt treatment of the person.

Figure 2:
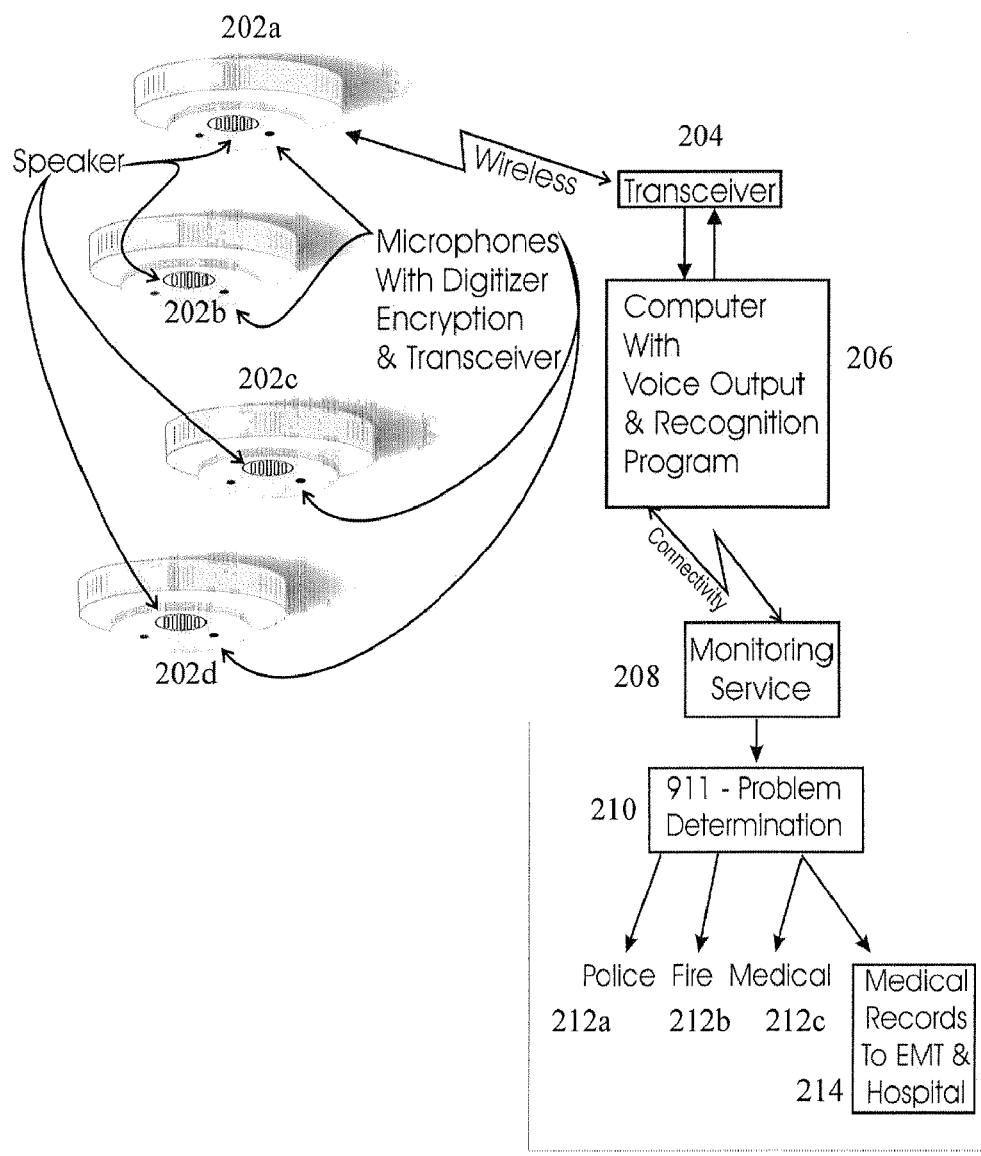
FIG. 2 is an example embodiment of a system for providing coordinated health monitoring, emergency response, and medical record delivery.

Referring now to FIG. 2, an example embodiment of a system 200 for providing coordinated health monitoring, emergency response, and medical record delivery, is shown. The system 200 can include one or more monitoring devices 202a-d and can also include a transceiver 204. The system 200 can further include one or more computing devices 206.

Operatively, when a patient is exhibiting the signs of an emergency, the one or more monitoring devices 204a-c can sense emergency-related indicators and data and can digitize and encrypt the data. The emergency-related indicators and data can then be transmitted wirelessly to a transceiver 204, which, in turn, send transmits the data to one or more computing devices 206, which contain a voice output and recognition program. The one or more computing devices analyze and interpret the data and send the data to a monitoring service 208 for validation. If an emergency is determined to exist, the monitoring service can alert emergency services 210, which can include police services 212a, fire services 212b, and medical services 212c. In the event of an emergency or otherwise, emergency personnel can be provided with a link to the records 214 of the person undergoing the emergency so as to enable more accurate treatment.

Figure 3:
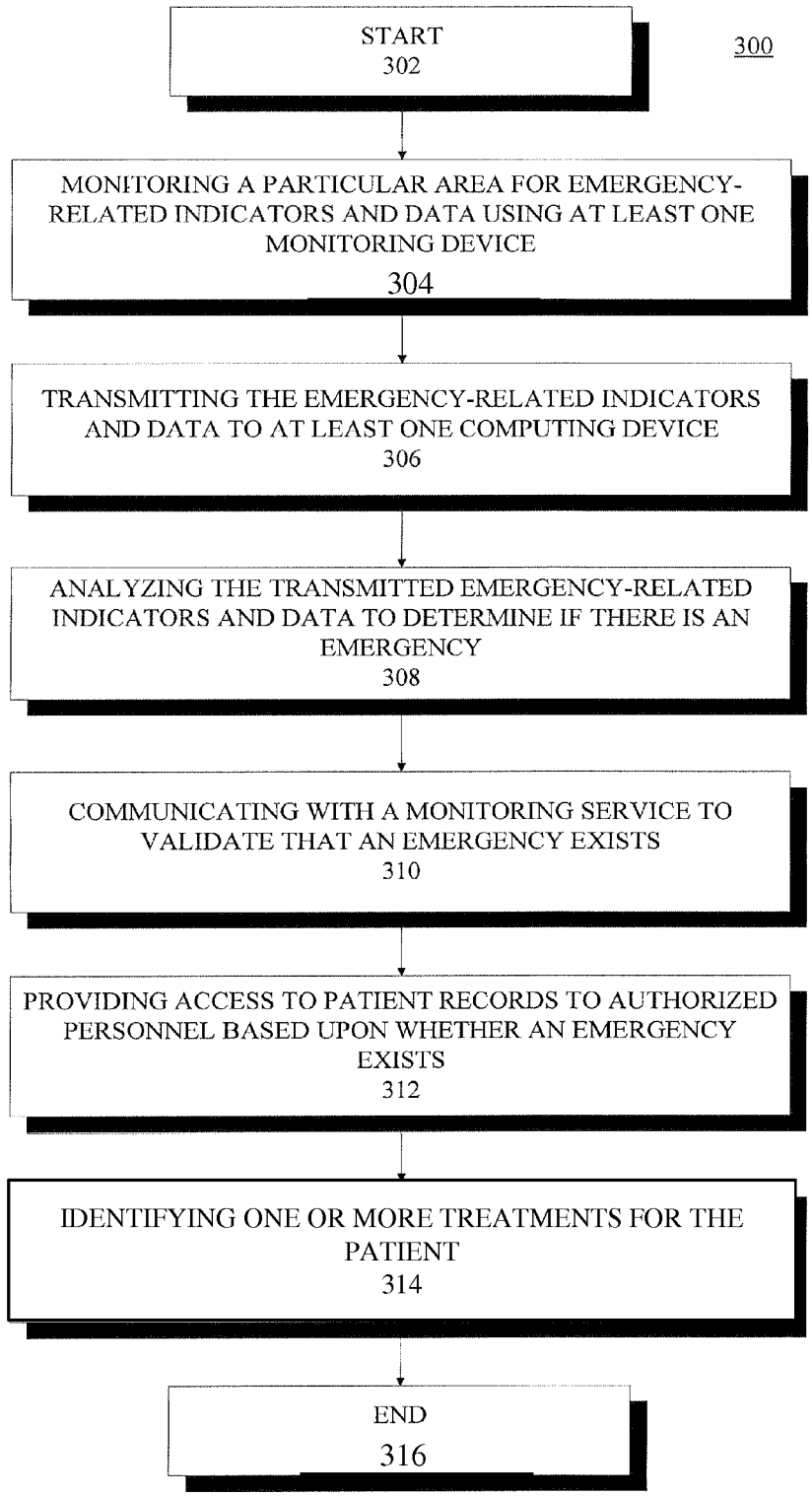
FIG. 3 is a flowchart of steps in a method for providing coordinated health monitoring, emergency response, and medical record delivery, according to another embodiment of the invention.

Referring now to FIG. 3, a flowchart is provided that illustrates certain method aspects of the invention. The flowchart depicts steps of a method 300 for providing coordinated health monitoring, emergency response, and medical record delivery. The method 300 illustratively includes, after the start at step 302, monitoring a particular area for emergency-related indicators and data by utilizing one or more monitoring devices at step 304. The one or more monitoring devices detect one or more among speech, sounds, images, and other detectable emergency-related indicators. The method 300 also includes transmitting the emergency-related indicators and data to one or more computing devices, wherein the one or more computing devices are communicatively linked to the one or more monitoring devices at step 306. Additionally, the method 300 includes at step 308 analyzing the transmitted emergency-related indicators and data to determine whether there is an emergency, the analysis being performed by the one or more computing devices. The method 300 also includes communicating with a monitoring service to validate that an emergency exists at step 310. The method 300 further includes at step 312 providing access to patient records to authorized personnel, based upon whether an emergency exists. In some embodiments, the system can be configured so that in addition to release patient records, treatment options are also identified at optional step 314, based on the outcomes of similar patients. This is discussed in greater detail below. The method 300 illustratively concludes at step 316.

The method 300 can also include, at the monitoring step 304, utilizing health-monitoring sensors, wherein the health-monitoring sensors can detect one or more among blood pressure, temperature, heart-rate, and other health-related patient metrics. For example, if a person is undergoing an emergency which does not cause the person to make a sound or move around, the health-monitoring sensors could enable detection of other signs of an impending emergency, such as elevated blood pressure, rapid heart rate, and high body temperature.

According to another embodiment, the method 300 can further include communicatively linking to emergency services and signaling an alarm to indicate that an emergency is occurring. By enabling a link to emergency services and signaling an alarm, emergency personnel and/or others in the vicinity of the person undergoing the emergency can quickly respond to the emergency and administer treatment. In one embodiment, the method 300 can include storing and forwarding a record of the emergency-related indicators and data to at least one of the monitoring service and an emergency service. For example, when the monitoring device senses emergency-related indicators and data, such as speech, images, or sounds, the data can be stored for future use and analysis and forwarded to emergency services and/or physicians for use.

According to yet another embodiment, the method 300 can include integrating drug dispensing devices, wherein the drug dispensing devices administer drugs so as to enable remote medical maintenance and assistance. As a result, those undergoing emergencies can receive prompter and more effective treatment so as to minimize the effects of an emergency.

In some embodiments, members of a group may be itinerant between facilities or other locations where monitoring devices and sensors are located. Thus, the individuals may be recognized at each of the locations by various means for purposes of the monitoring and transmitting at steps 304 and 306 in method 300. In some embodiments, biometric sensors can be used to recognize the individuals. These include, but are not limited to, devices and systems for facial recognition, voice recognition, and retinal identification. In other embodiments, recognition of individuals can be based on objects in possession of or otherwise associated with the individual and appropriate systems and devices can be provided at each of the locations. These include, but are not limited to, system and devices for remotely reading machine readable codes embedded in identification objects. Examples include, but are not limited to, active or passive radio-frequency identification (RFID) devices or optically scanning machine readable codes. In some embodiments, different systems and devices can be provided at each of the locations. For such locations, the object in possession of the individual can have various types of machine readable code incorporated therein. Alternatively, some locations can utilize a combination of biometric and machine readable code for identification. That is, in addition to reading the machine readable code, identification can also require acquiring biometric information. Thus, the combination operates as a username and password for unlocking information regarding the individual.

Although the machine readable codes in the identification objects can be passive in some embodiments, these codes can vary over time in other embodiments. For example, in some embodiments, the machine readable code in the identification objects can be configured to denote changes in the medical state of and individual. Examples of various methods for implementing varying machine code are illustrated in U.S. patent application Ser. No. 13/302,557, filed Nov. 22, 2011, the contents of which are herein incorporated by reference in their entirety. In some specific embodiments, the identification object can include or can communicate with a sensor that detects changes of the state of health of the individual. Such information may be used to predict the probability of a need for medical assistance and even stage preparations for timely administration nearby.

For example a barcode worn on the exterior of an individual may indicate a change in the status of health contained within the individual and wellness changes. Some examples include, but are not limited to, body temperature, heart rate, blood pressure, recent exertion, injury, environmental stresses or even radiation exposure. In some cases, the type of information can be selected based on demographic or geographic information. For example, for individuals in different age groups, the types of information that should be available during most emergencies can vary. Accordingly, the information directly available and that is immediately accessible can vary. In another example, the type of information can depend on the abilities of the first responders in the individual's community. Thus, when responders in a community have access to advanced life support equipment, information relevant to the use of such equipment for the patient can be stored.

The monitoring equipment normally used for one individual, could be serially re-used for multiple individuals, each separately recognized. This provides two benefits. First, facilities for treatment, provider offices, hospitals, and even emergency equipment could be aware of the individuals contained within the facilities. Second, these same entities can assemble or be used for assembling data for public health situations. For example, excluding individuals who may exacerbate illness in other, identifying individuals susceptible to communicable disease, or identifying carriers of communicable disease or hazardous substances.

Although the foregoing describes how the various embodiments can assist in the identification of an individual presenting himself for medical treatment, in the case of communicable disease or exposure to hazardous substance, a primary concern is how to identify such individuals. Thus, in some embodiments, the analyzing, communicating, and providing of steps 308-312 in method 300 can be accomplished via the use of Episodic Social Networks, as described in International Patent Application No. PCT/US12/52404, filed Aug. 25, 2012, the contents of which are herein incorporated by reference in their entirety.

As noted in PCT/US12/52404, groups of people are naturally associated with one another via their activities and interactions. In particular, groups of people are associated with different episodes. Thus, by identifying the Episodic Social Networks that an individual is associated with, to some extent, past behavior of the individual can be characterized and future activities and interactions can be predicted or guided based on the history of individuals associated with the same episodes. Accordingly, in the case where an individual is identified at a facility with a communicable disease or exposure thereto, an analysis of treatments and outcomes for other individuals in the same or similar sets of episodes can be used to guide or identify treatment for the individual. Thus, the system can not only identify records of relevance based on the Episodic Social Networks associated with the patient, but also identify potential treatments. For example, if an individual is identified with a series of Episodic Social Networks, the outcomes of other individuals in the same Episodic Social Networks can be evaluated. Based on this analysis, a particular treatment can be identified. Alternatively, the various treatments for these other individuals can be ranked in order of success and presented. Thus, past experience with other individuals with the same or substantially similar Episodic Social Networks can be used to more accurately guide treatment of the individual in question.

Moreover, based on this same type of analysis, other individuals at the same facility and who may have been exposed to the communicable disease could be expeditiously treated, immunized, or quarantined based on the Episodic Social Networks they are associated with.

Additionally, the treatment for such individuals can be directed not only for preventing or treating the communicable disease in these identified individuals at the facility, but also to prevent them from spreading to other individuals they are predicted to interact with. In particular, the treatment can be adjusted if such individuals are predicted to interact with susceptible persons at home, at work, or other locations. In other words, the treatment can be selected for the individual, based on the Episodic Social Networks he is associated with, not only to provide the individuals with appropriate treatment, but also with guidance to prevent these individuals from becoming carriers of the communicable disease.

For example, future social connections could be temporarily suspended, by warning the individuals or adjusting social schedules as necessary. Where possible, communicable diseases could be limited in scope of infection for the public need in general. Tracking the casual or intimate associations and plans of individuals within social networks is well within the abilities of modern data processing equipment, networking and databases. In such cases, integration of information from various disparate sources, including medical and non-medical sources, might be necessary. The integration of such information can be accomplished in a manner similar to that described in PCT/US12/52404.

Moreover, individuals may allow such a system to plan for maximum wellness, by avoiding contact with potential sources of infection, planning immunizations when contact with such sources is probable or unavoidable, planning sequential associations with members of affinity groups similarly dedicated to planning for maximum wellness, physical well being, preemptive inoculation and avoidance of potential infection.

Still another variation might utilize the concepts of positive identification, as described in U.S. Provisional Patent Application No. 61/635,910, filed Apr. 20, 2012, the contents of which are herein incorporated by reference in their entirety. This can be used to assure that individuals, with whom close or intimate contact is potential, are who they say they are and similarly, well according to a common database. This could be especially useful in the control of the spread of socially transmitted diseases and the avoidance of those diseases by specific individuals, groups or industries.

Some of the concepts described above may seem counter to the rights of privacy. Accordingly, in some embodiments of the invention, the information can be collected and utilized with safeguards to assure an individual's information remains anonymous. For example, prior to uploading particular information for analysis with respect to Episodic Social Networks, identifying information can be removed, encrypted, or otherwise obfuscated to prevent access to information. In the case of encrypted or obfuscated information, additional safeguards (e.g., additional passwords) can be utilized to allow access in certain situations.

Another privacy concern is with regards to which records to locate and release in an emergency situation. For example, a patient's enrollment in a drug treatment program is often shielded from their general records by law. While a medical records system might block prescription of certain drugs (e.g. morphine based painkillers, tranquilizers, etc) to individuals in such programs, in an emergency the patient's privacy would become subordinate to treatment of a life threatening scenario. Accordingly, another aspect of the various embodiments is that the type of emergency might dictate what records to release to the medical team and specifically which members of the team may view them. An anesthesiologist might have critical need to know of a drug treatment history, even a dentist, where another specialty may have less need. Thus, in the various embodiments, a set of release rules can be provided to govern when and to who records are released. Further, such rules can be based on the history of Episodic Social Networks associated with an individual.

As noted above, the medical histories of patients, particularly treatment programs might be seen as Episodic Social Networks. Thus, even though two patients might be associated with same type of emergency, the Episodic Social Networks might be distinct for each patient. Accordingly, the relevance of particular portions of the histories for two patients can vary. Therefore, rather than releasing the same types of records for both patients, a methodology in accordance with the various embodiments could decide to release two different sets of records for the two patients. That is, a system in accordance with the various embodiments can include logic that determines the most relevant set of records for a patient or group of patients associated with a particular set of Episodic Social Networks.

In some embodiments, records could be ranked by relevance to a particular injury or medical condition. For example, a dental history of plaque and gingivitis may be of particular significance to a cardiologist in the event of a heart attack or other medical condition, as the same methodology produces both dental plaque and arterial plaque. Thus, only histories with a minimum ranking are released when the physician identifies the type of injury.

In some embodiments, records could be ranked by relevance to a particular specialty. For example, a dental history of plaque and gingivitis may be of particular significance to a cardiologist, as the same methodology produces both dental plaque and arterial plaque. Thus, only histories with a minimum ranking are released when the physician identifies his specialty.

In other embodiments, particular records can be identified for release only when a particular set of Episodic Social Networks are associated with the patient. For example, in the case of dental history, normally such history might not be relevant for the case of a fracture and thus might not be ranked highly for the treating physician or the type of injury. However, in the case of a senior citizen, dental work may have put the patient at a higher risk of infection or other conditions. Thus in the case where there has been dental work followed by a traumatic injury, such as the fracture, the records would be released to note to the treating physician that there is an increased risk of infection.

In other words, if the history warrants, certain records are released that normally would not be released. For example, a patient in a drug treatment program might have that history become part of the general patient record if the patient were admitted for a drug overdose. Further, the question may be whether there are any other records that need to be recorded, or other tests and diagnosis that need to be created.

In some embodiments, a patient history, expressed or stored as a set of Episodic Social Networks, could assist in determining if an emergency exists and which type of emergency would be more likely. For example, an individual with a history of depression and drug treatment might guide the medical team to look toward a (potentially self administered) drug overdose.

Therefore, based on the history conveyed by the Episodic Social Networks, the indicators could be used to initially determine that an emergency potentially exists. Thereafter, the Episodic Social Networks can be used to determine if it really exists or not based on patient history. That is, in some cases, a particular history for two different patients, combined with the indicators, may result in an emergency situation for one but not for the other. Alternatively, it can be used to prioritize cases in a triage situation. That is, the histories may indicate that a same emergency situation for two patients may only be life threatening (or less life threatening) to one patient.

Further, should a patient give permission to collect otherwise private personal records in a probable emergency, information could be collected in advance and held secure within the system to be available for immediate use during an emergency. An affinity group that included risky lifestyle choices such as smoking, indolence, heavy alcohol use, or diseases such as diabetes or obesity could reach a threshold where a potential emergency situation might be deemed imminent. In such case, specific specialties, such as cardiology might be alerted, where a specialty, less likely to be required in the anticipated emergency (eg dermatology) would not be alerted.

Membership in potential affinity groups and ESNs following potential algorithms for anticipating an emergency (especially if the patient authorizes in advance) can be used to compare the individuals to peers within their groups and report back to care team on probability of an existing or imminent emergency.

Further, if genetic information is reduced to group individuals into affinity groups for susceptibility to certain diseases, wellness deterioration, or perhaps superior immune response that could be a factor in determining the probability of an existing or imminent emergency. Membership in a specific affinity group may also help associate symptoms and cause in forming a diagnosis, where disease progression for a set of individuals following a specific lifestyle or health history is expressed as a series of Episodic Social Networks in the form of prior diagnosis, susceptibilities, responsiveness to care, or lifestyle profiles.

Another situation where an emergency situation would override patient privacy would be in the release of genetic information from an otherwise secure history of adoption, out of wedlock births, half siblings and the like. Potentially, genetic information may eventually be used to reconstruct accurate family histories. In the case of specific inherited disorders—the medical histories of relatives, descendents and ancestors may become relevant in an emergency situation and be released conditionally. Indeed, members of a family may be considered as an affinity group, with ancestry defined as Episodic Social Networks, such that inherited or shared genetic traits would become relevant in an emergency. For example, members of a family may jointly release private medical information if another member of the family has a declared emergency—such as a coronary artery blockage. The health information system could pre-trace and hold secure the family relationships, even those not known to the family and then determine by data mining or other means that the family has a probable inherited trait that would be useful in an emergency diagnosis. In such an emergency, the family history and true ancestry and all actual siblings, relatives, descendents be notified of the susceptibility afterward. This could be true, even in cases of drug dependency or psychiatric histories that would otherwise be held secret. People with specific susceptibilities to food, tobacco, alcohol abuse as well as individuals with the above drug dependency, psychiatric, genetic and lifestyle profile, specific diseases and the like could be grouped into affinity groups and tracked by Episodic Social Networks to verify and select which individuals or groups are most at risk. This could also be effective in tracking individuals or groups with communicable or social diseases and determining which individuals are most at risk when considering other factors. One individual, whose medical history expressed as a series of Episodic Social Networks for maladies, treatment, and susceptibilities might be at risk (perhaps with a history of diabetes, certain social diseases, etc) where another individual might be less at risk.

The above categorization could also be used to track which individuals had similar progress or lack of progress with given treatments again when coupled with similar genetic profile, similar lifestyle profile or other groupings in ESNs to evaluate therapies and drugs and make decision to migrate to more effective strategies and share identified and de-identified data for analysis of therapy effectiveness.

The Episodic Social Network patterns would then help spot critical situations in individuals, likelihood of emergency by Episodic Social Network sequence or structure to help determine predictable emergency situations by the above profiles.

The invention can be realized in hardware, software, or a combination of hardware and software. The invention can be realized in a centralized fashion in one computer system, or in a distributed fashion where different elements are spread across several interconnected computer systems. Any type of computer system or other apparatus adapted for carrying out the methods described herein is suitable. A typical combination of hardware and software can be a general purpose computer system with a computer program that, when being loaded and executed, controls the computer system such that it carries out the methods described herein.

The invention, as already mentioned, can be embedded in a computer program product, such as magnetic tape, an optically readable disk, or other computer-readable medium for storing electronic data. The computer program product can comprise computer-readable code, (defining a computer program) which when loaded in a computer or computer system causes the computer or computer system to carry out the different methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The preceding descriptions of preferred embodiments of the invention have been presented for the purposes of illustration. The description provided is not intended to limit the invention to the particular forms disclosed or described. Modifications and variations will be readily apparent from the preceding description. As a result, it is intended that the scope of the invention not be limited by the detailed description provided herein.

We claim:

1. A computer-based method for medical record delivery, the method comprising the steps of:
   receiving a request for records associated with a patient;
   based on at least one an episodic social network model and a stored patient profile of health and wellness of the patient, identifying one or more episodic social networks (ESNs) associated with the patient;
   based on a set of release rules, the request, and the ESNs associated with the patient, selecting one or more portions of the patient profile to release to the requestor.

2. The method of claim 1, further comprising:
   based on the episodic social network model, the stored patient profile of health and wellness of the patient, and a current health and wellness of the patient, identifying one or more future ESNs associated with the patient; and
   recommending a treatment protocol for the patient based on the future ESNs.

3. The method of claim 1, wherein the request comprises a diagnosis for the patient, wherein each portion of the patient profile is associated with at least one diagnosis, and wherein the set of release rules specifies releasing at least a portion of the patient profile associated with the diagnosis in the request.

4. The method of claim 1, wherein the request comprises a medical specialty of the requestor, wherein each portion of the patient profile is associated with at least one medical specialty, and wherein the set of release rules specifies releasing at least a portion of the patient profile associated with the medical specialty in the request.

5. The method of claim 1, further comprising:
   identifying one or more other patients exposed to the patient;
   repeating the receiving, identifying, and selecting for each of the other patients, wherein the ESNs associated with each of the other patients comprise past, current, and future ESNs; and
   generating a treatment protocol for each of the other patient based on corresponding ones of the future ESNs.

6. The method of claim 1, further comprising collecting health and wellness information for the patient based on at least one of biometric data associated with the patient and machine-readable code embedded in an identifying object associated with the patient.

7. The method of claim 6, wherein the machine readable code in the identifying object is configured to vary in response to changes in the current health and wellness of the patient.

8. A system for medical record delivery, comprising:
   a processor;
   a computer readable medium comprising a plurality of code sections for causing the processor to perform the steps of:
      receiving a request for records associated with a patient;
      based on at least one an episodic social network model and a stored patient profile of health and wellness of the patient, identifying one or more episodic social networks (ESNs) associated with the patient;
      based on a set of release rules, the request, and the ESNs associated with the patient, selecting one or more portions of the patient profile to release to the requestor.

9. The system of claim 8, the computer readable medium further comprising code sections for causing the processor to perform the steps of:
   based on the episodic social network model, the stored patient profile of health and wellness of the patient, and a current health and wellness of the patient, identifying one or more future ESNs associated with the patient; and
   recommending a treatment protocol for the patient based on the future ESNs.

10. The system of claim 8, wherein the request comprises a diagnosis for the patient, wherein each portion of the patient profile is associated with at least one diagnosis, and wherein the set of release rules specifies releasing at least a portion of the patient profile associated with the diagnosis in the request.

11. The system of claim 8, wherein the request comprises a medical specialty of the requestor, wherein each portion of the patient profile is associated with at least one medical specialty, and wherein the set of release rules specifies releasing at least a portion of the patient profile associated with the medical specialty in the request.

12. The system of claim 8, the computer readable medium further comprising code sections for causing the processor to perform the steps of:
   identifying one or more other patients exposed to the patient;
   repeating the receiving, identifying, and selecting for each of the other patients, wherein the ESNs associated with each of the other patients comprise past, current, and future ESNs; and
   generating a treatment protocol for each of the other patient based on corresponding ones of the future ESNs.

13. The system of claim 1, the computer readable medium further comprising code sections for causing the processor to perform the step of:
   collecting health and wellness information for the patient based on at least one of biometric data associated with the patient and machine-readable code embedded in an identifying object associated with the patient.

14. A non-transitory computer-readable medium having stored thereon a plurality of code sections for causing a computing device to perform a method for medical record delivery, the method comprising the steps of:
   receiving a request for records associated with a patient;
   based on at least one an episodic social network model and a stored patient profile of health and wellness of the patient, identifying one or more episodic social networks (ESNs) associated with the patient;
   based on a set of release rules, the request, and the ESNs associated with the patient, selecting one or more portions of the patient profile to release to the requestor.

15. The non-transitory computer-readable medium of claim 14, wherein the method further comprises:
   based on the episodic social network model, the stored patient profile of health and wellness of the patient, and a current health and wellness of the patient, identifying one or more future ESNs associated with the patient; and
   recommending a treatment protocol for the patient based on the future ESNs.

16. The non-transitory computer-readable medium of claim 14, wherein the request comprises a diagnosis for the patient, wherein each portion of the patient profile is associated with at least one diagnosis, and wherein the set of release rules specifies releasing at least a portion of the patient profile associated with the diagnosis in the request.

17. The non-transitory computer-readable medium of claim 14, wherein the request comprises a medical specialty of the requestor, wherein each portion of the patient profile is associated with at least one medical specialty, and wherein the set of release rules specifies releasing at least a portion of the patient profile associated with the medical specialty in the request.

18. The non-transitory computer-readable medium of claim 14, wherein the method further comprises:
   identifying one or more other patients exposed to the patient;
   repeating the receiving, identifying, and selecting for each of the other patients, wherein the ESNs associated with each of the other patients comprise past, current, and future ESNs; and
   generating a treatment protocol for each of the other patient based on corresponding ones of the future ESNs.

19. The non-transitory computer-readable medium of claim 14, wherein the method further comprises collecting health and wellness information for the patient based on at least one of biometric data associated with the patient and machine-readable code embedded in an identifying object associated with the patient.

* * * * *